US009475763B2

(12) United States Patent
Liu et al.

(10) Patent No.: US 9,475,763 B2
(45) Date of Patent: Oct. 25, 2016

(54) PHOTORESIST COMPRISING NITROGEN-CONTAINING COMPOUND (71) Applicant: Rohm and Haas Electronic Materials, LLC, Marlborough, MA (US)

(72) Inventors: Cong Liu, Shrewsbury, MA (US); Chunyi Wu, Shrewsbury, MA (US); Gerhard Pohlers, Needham, MA (US); Gregory P. Prokopowicz, Worcester, MA (US); Cheng-Bai Xu, Southboro, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 14/589,759

(22) Filed: Jan. 5, 2015

(65) Prior Publication Data
US 2015/0353482 A1 Dec. 10, 2015

Related U.S. Application Data (62) Division of application No. 13/013,780, filed on Jan. 25, 2011, now Pat. No. 8,927,190.

(60) Provisional application No. 61/336,762, filed on Jan. 25, 2010.

(51) Int. Cl.
*G03F 7/004* (2006.01)
*C07C 271/16* (2006.01)
(Continued)

(52) U.S. Cl.
CPC .......... *C07C 271/16* (2013.01); *G03F 7/0045* (2013.01); *G03F 7/0382* (2013.01);
(Continued)

(58) Field of Classification Search
CPC ...... G03F 7/0397; G03F 7/11; G03F 7/2041; G03F 7/0045; G03F 7/0382; G03F 7/0392; C07C 271/16
USPC ............... 430/270.1, 322, 325, 913; 560/160
See application file for complete search history.

(56) References Cited

U.S. PATENT DOCUMENTS

| 6,673,511 B1 | 1/2004 | Hatakeyama et al. | |
|---|---|---|---|
| 7,629,106 B2* | 12/2009 | Hatakeyama | G03F 7/0045 430/270.1 |
| 2004/0106063 A1* | 6/2004 | Hatakeyama | G03F 7/0045 430/270.1 |

FOREIGN PATENT DOCUMENTS

| CN | 101040220 A | 9/2007 |
|---|---|---|
| EP | 1253138 A2 | 10/2002 |

(Continued)

OTHER PUBLICATIONS

Khaksar etal, "Hydrogen bond catalyzed chemoselective N-tert-butoxycarbonylation of amines", Tetrahedron Letters, May 19, 2008, vol. 49, No. 21. pp. 3527-3529.*

(Continued)

*Primary Examiner* — Amanda C Walke
(74) *Attorney, Agent, or Firm* — Mintz Levin Cohn Ferris Glovsky and Popeo, P.C.; Peter F. Corless (57) ABSTRACT

New nitrogen-containing compounds are provided that comprise multiple hydroxyl moieties and photoresist compositions that comprise such nitrogen-containing compounds. Preferred nitrogen-containing compounds comprise 1) multiple hydroxyl substituents (i.e. 2 or more) and 2) one or more photoacid-labile groups.

22 Claims, 1 Drawing Sheet

(51) Int. Cl.
- *G03F 7/038* (2006.01)
- *G03F 7/039* (2006.01)
- *G03F 7/11* (2006.01)
- *G03F 7/20* (2006.01)
- *G03F 7/16* (2006.01)
- *G03F 7/32* (2006.01)

(52) U.S. Cl.
CPC ........... *G03F 7/0392* (2013.01); *G03F 7/0397* (2013.01); *G03F 7/11* (2013.01); *G03F 7/16* (2013.01); *G03F 7/20* (2013.01); *G03F 7/2041* (2013.01); *G03F 7/32* (2013.01)

(56) References Cited

FOREIGN PATENT DOCUMENTS

| EP | 1640804 A2 | 3/2006 | |
| --- | --- | --- | --- |
| JP | EP 1640804 A2 * | 3/2006 | ........... G03F 7/0045 |
| JP | 2010134126 A | 6/2010 | |
| WO | 2005098542 A1 | 10/2005 | |
| WO | 2006040921 A1 | 4/2006 | |
| WO | 2010061774 A1 | 6/2010 | |

OTHER PUBLICATIONS

Machine translation of JP 2010134126 A.

Khaksar, S., et al, "Hydrogen bond catalyzed chemo selective N-tert-butoxycarbonylation of amines", Tetrahedron Letters, May 19, 2008, pp. 3527-3529, vol. 49, No. 21, Elsevier, Amsterdam, NL.

Clinch, Keith et al, "Third-generation immucillins: Syntheses and bioactivities of acyclic immucillin inhibitors of human purine nucleoside phosphorylase", Journal of Medicinal Chemistry, Feb. 26, 2009, pp. 1126-1143, vol. 52.

English Language Summary of Office Action of Counterpart Japanese Patent Application No. 2012-000226—Dispatch Date: Sep. 17, 2015 (2 Pages).

English Language Summary of Office Action of Counterpart Taiwan Patent Application No. 102-2(6) 01205-10221523300—Date: Nov. 7, 2013 (4 Pages).

* cited by examiner

PHOTORESIST COMPRISING NITROGEN-CONTAINING COMPOUND

The present application is a divisional application of U.S. application Ser. No. 13/013,780, filed Jan. 25, 2011, which claims the benefit of U.S. provisional patent application No. 61/336,792, filed Jan. 25, 2010, which applications are incorporated therein by reference in their entirety.

This invention relates to new nitrogen-containing compounds that comprise multiple hydroxyl moieties and photoresist compositions that comprise such nitrogen-containing compounds. Preferred nitrogen-containing compounds comprise 1) multiple hydroxyl substituents (i.e. 2 or more) and 2) one or more photoacid-labile groups.

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of basic compounds have been reported for use in photoresist compositions. See, e.g., U.S. Pat. Nos. 6,607,870 and 7,379,548.

In one aspect, we now provide novel nitrogen-containing compounds for use in both positive-acting and negative-acting photoresist compositions. Photoresists of the invention suitably may comprise one or more resins (resin component) and one or more one or more photoacid generator compounds (photoacid generator or PAG component) in addition to one or more nitrogen-containing compounds (nitrogen-containing component).

Preferred nitrogen-containing compounds of the invention for use in photoresists may comprise 1) two or more hydroxyl substituents and 2) one or more photoacid-labile groups. Typical photoacid-labile groups undergo bond-breaking in the presence of exposure-generated acid in a photoresist layer, during lithographic processing of the photoresist (including e.g. during post-exposure baking of the photoresist layer).

We have surprisingly found that use of nitrogen-containing compounds as disclosed herein in a photoresist composition, including chemically-amplified photoresist compositions, can significantly enhance resolution of a relief image (e.g. fine lines) of the resist. In particular, we have found that including a second (or more than 2) hydroxyl groups on an nitrogen-containing compound can impart significantly enhanced lithographic results, including relative to a comparable photoresist that is otherwise identical to the photoresist containing a multi-hydroxy nitrogen-containing compound of the invention, but where in the comparative photoresist the nitrogen-containing compound has only a single hydroxyl moiety. See, for instance, the comparative data set forth in Examples 5 and 6, which follow.

Without being bound by theory, nitrogen-containing compounds as disclosed herein can function as quencher elements in a photoresist and restrict migration (diffusion) of photogenerated acid (in the case of a positive-acting resist) out of exposed regions and into unexposed regions which migration could compromise resolution of the image patterned into the resist layer.

Preferred nitrogen-containing compounds of the invention for use in photoresists may be polymeric or non-polymeric, with non-polymeric materials preferred for many applications. Preferred nitrogen-containing compounds have relatively low molecular weight, e.g. la molecular weight of less than 3000, or even less such as a molecular weight of less than 2500, 2000, 1500, 1000, 800 or 500.

Particularly preferred nitrogen-containing compounds of the invention for use in photoresists include nitrogen-containing compounds represented by the following Formula (I):

wherein $R^1$ and $R^2$ are the same or different and at least one of $R^1$ and $R^2$ is other than hydrogen, and together $R^1$ and $R^2$ comprise at least two hydroxyl groups (i.e. $R^1$ may comprise at least two hydroxyl groups; $R^2$ may comprise at least two hydroxyl groups; or $R^1$ may comprise at least one hydroxyl group and $R^2$ may comprise at least one hydroxyl group), or $R^1$ and $R^2$ may be taken together to form a ring where the $R^1/R^2$ ring (including substituents thereof) comprises at least 2 hydroxy groups; and X comprises a photoacid-labile group, such as a photoacid-labile ester or acetal group.

Preferred $R^1$ and $R^2$ groups include hydrogen and optionally substituted alkyl, carbocyclic aryl (e.g. phenyl, naphthyl), and the like where the moieties include hydroxyl substitution (e.g. hydroxyalkyl having 1 to 20 carbon atoms). If $R^1$ and $R^2$ are taken together to form a cyclic structure with the -nitrogen, where the cyclic structure comprises two or more hydroxyl groups.

In certain preferred embodiments, $R^1$ or $R^2$ is hydrogen, and the non-hydrogen group comprises at least two hydroxyl groups, such as nitrogen-containing compounds of the following Formula (IIA).

wherein in Formula (IIA) $R^{1'}$ is a non-hydrogen substituent that contains at least 2 hydroxy groups such as $C_{1-25}$alkyl that has two or more hydroxyl group ad the like; and X is the same as defined for Formula (I) above i.e. a photoacid-labile group, such as a photoacid-labile ester or acetal group.

In additional preferred embodiments, preferred nitrogen-containing compounds comprise a photoacid-labile ester group, such as compounds of the following Formula (IIB).

(IIB)

wherein in Formula (BB) $R^1$ and $R^2$ are the same as defined as defined in Formula (I); and $R_1$, $R_2$ and $R_3$ each independently represent an optionally substituted straight, branched or cyclic group of 1 to 30 carbon atoms.

Additional preferred nitrogen-containing compounds include those of the following Formula (IIC):

(IIC)

wherein $R_1$, $R_2$ and $R_3$ each independently represent an optionally substituted straight, branched or cyclic group of 1 to 30 carbon; $R_4$ represents hydrogen or a straight, branched or cyclic group of 1 to 30 carbon; m1, m2 and m3 are each independently an integer of 0 to 30; n1, n2 and n3 are each independently an integer of 0 or 1; at least two among n1, n2 and n3 are 1.

Still additional preferred nitrogen-containing compounds include those of the following Formula (IID):

(IID)

wherein $R_1$, $R_2$ and $R_3$ each independently represent a straight, branched or cyclic group of 1 to 30 carbon; $R_4$ represents hydrogen or an optionally substituted straight, branched or, cyclic group of 1 to 30 carbon; n is an integer of 1 to 30; and n is a positive integer e.g. from 1 to 20.

Exemplary specifically preferred nitrogen-containing compounds for use in photoresists include the following structures A, B, C, D, E and F. As should be understood, in the below structures as well as elsewhere herein, the designation "t-BOC" refers to the moiety-$(C=O)OC(CH_3)_3$.

A

B

C

D

E

F

Preferably, nitrogen-containing compounds of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Preferred imaging wavelengths of photoresists of the invention include sub-300 nm wavelengths e.g. 248 nm, and sub-200 nm wavelengths e.g. 193 nm and EUV.

Particularly preferred photoresists of the invention contain an imaging-effective amount of one or more PAGs and a nitrogen-containing component as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups;

2) a resin that is substantially or completely free of phenyl groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. No. 5,843,624 incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083. Polymers of this type may contain in preferred aspects certain aromatic groups such as hydroxynaphthyl.

Resists of the invention also may comprise a mixture of distinct PAGs, typically a mixture of 2 or 3 different PAGs, more typically a mixture that consists of a total of 2 distinct PAGs.

The invention also provide methods for forming relief images of the photoresists of the invention, including methods for forming highly resolved patterned photoresist images (e.g. a patterned line having essentially vertical sidewalls) of sub-quarter micron dimensions or less, such as sub-0.2 or sub-0.1 micron dimensions.

The invention further provides articles of manufacture comprising substrates such as a microelectronic wafer or a flat panel display substrate having coated thereon the photoresists and relief images of the invention. Other aspects of the invention are disclosed infra.

Photoresists of the invention may comprise one or more hydroxyl nitrogen-containing compounds in a wide amount range. The added hydroxy nitrogen-containing component is suitably used in relatively small amounts, e.g. about 0.5 to 10 or 15 percent by weight relative to the PAG, more typically 1 to about 5, 6, 7, 8, 9 or 10 weight percent.

Nitrogen-containing compounds as disclosed herein can be readily synthesized. For instance, a nitrogen-containing polyol compounds can be reacted to provide a pendant photoacid-labile ester or acetal group. See, for instance, the syntheses of Examples 1 and 2, which follow. Many reagents to form desired nitrogen-containing compounds are commercially available.

As stated herein, various substituent groups of nitrogen-containing compounds of the invention may be optionally substituted. Substituted moieties are suitably substituted at one or more available positions by, e.g., halogen such as F, Cl Br and/or I, nitro, cyano, sulfono, alkyl including $C_{1-16}$ alkyl with $C_{1-8}$ alkyl being preferred, haloalkyl such as fluoroalkyl (e.g. trifluoromethyl) and perhaloalkyl such as perfluoro$C_{1-4}$alkyl, alkoxy including $C_{1-16}$ alkoxy having one or more oxygen linkages with $C_{1-8}$ alkoxy being preferred, alkenyl including $C_{2-12}$ alkenyl with $C_{2-8}$ alkenyl being preferred, alkenyl including $C_{2-12}$ alkenyl with $C_{2-8}$ alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthracenyl and naphthyl.

As used herein, the term alkyl, alkenyl and alkynyl unless otherwise modified refers to both cyclic and noncyclic groups, although of course cyclic groups will comprise at least three carbon ring members. Alkenyl and alkynyl groups of compounds of the invention have one or more unsaturated linkages, typically 1 to about 3 or 4 unsaturated linkages. Also, the terms alkenyl and alkynyl as used herein refer to both cyclic and noncyclic groups, although straight or branched noncyclic groups are generally more preferred. Alkoxy groups of PAG compounds of the invention have one or more oxygen linkages, typically 1 to about 5 or 6 oxygen linkages. Alkylthio groups of PAGs of the invention have one or more thioether linkages, typically 1 to about 5 or 6 thioether linkages. Alkylsulfinyl groups of PAG compounds of the invention have one or more sulfinyl (SO) linkages, typically 1 to about 5 or 6 sulfinyl linkages. Alkylsulfonyl groups of PAG compounds of the invention have one or more sulfonyl ($SO_2$) linkages, typically 1 to about 5 or 6 sulfonyl linkages. Preferred alkylamino groups of PAG compounds of the invention include those groups having one or more primary, secondary and/or tertiary amine groups, preferably 1 to about 3 or 4 amine groups. Suitable alkanoyl groups have one or more carbonyl groups, typically 1 to about 4 or 5 carbonyl groups. Alkoxy, alkylthio, alkylsulfinyl, alkylsulfonyl, alkanoyl and other groups may be suitably either linear or branched. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S). Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, As discussed, photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution.

Preferably, a photoacid generator compound of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

PAGs of the invention also are preferably used with polymers that contain one or more photoacid-labile groups and that are substantially, essentially or completely free of phenyl groups. Such photoresist compositions are particularly useful for imaging with sub-200 nm radiation such as 193 nm radiation. As mentioned above, such resins of this type may in preferred aspects comprise certain aromatic groups such as hydroxy naphthyl.

For example, preferred polymers contain less than about 5 mole percent aromatic groups, more preferably less than about 1 or 2 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups, Aromatic groups can be highly absorbing of sub-200 nm radiation and thus are undesirable for polymers used in photoresists imaged with such short wavelength radiation.

Suitable polymers that are substantially or completely free of aromatic groups and may be formulated with a PAG of the invention to provide a photoresist for sub-200 nm imaging are disclosed in European application EP930542A1 of the Shipley Company.

Suitable polymers that are substantially or completely free of aromatic groups suitably contain acrylate units such as photoacid-labile acrylate units as may be provided by polymerization of methyladamanatylacrylate, methyladamanylmethacrylate, ethylfencylacrylate, ethylfencylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride; and the like.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention. Such compositions and the use thereof has been disclosed in European Patent Applications 0164248 and 02329.72 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

As discussed above, photoresists for use in the invention also comprise a photoacid generator (i.e. "PAG") that is suitably employed in an amount sufficient to generate a latent image in a coating layer of the resist upon exposure to activating radiation. Preferred PAGs for imaging at 193 nm and 248 nm imaging include imidosulfonates such as compounds of the following formula:

wherein R is camphor, adamantane, alkyl (e.g. $C_{1-12}$ alkyl) and fluoroalkyl such as fluoro($C_{1-18}$alkyl) e.g. $RCF_2$— where R is optionally substituted adamantyl.

Also preferred is a triphenyl sulfonium PAG, complexed with anions such as the sulfonate anions mentioned above, particularly a perfluoroalkyl sulfonate such as perfluorobutane sulfonate.

Other known PAGS also may be employed in the resists of the invention. Particularly for 193 nm imaging, generally preferred are PAGS that do not contain aromatic groups, such as the above-mentioned imidosulfonates, in order to provide enhanced transparency.

Other suitable photoacid generators for use in present photoresists include for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, nitrobenzyl derivatives, for example, 2-nitrobenzyl p-toluenesulfonate, 2,6-dinitrobenzyl p-toluenesulfonate, and 2,4-dinitrobenzyl p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenensulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. One or more of such PAGs can be used.

Photoresists of the invention also may contain other materials. For example, other optional additives include actinic and contrast dyes, anti-striation agents, plasticizers, speed enhancers, sensitizers, etc. Such optional additives typically will be present in minor concentration in a photoresist composition except for fillers and dyes which may be present in relatively large concentrations such as, e.g., in amounts of from 5 to 30 percent by weight of the total weight of a resist's dry components.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; propionates, particularly methyl propionate and ethyl propionate; a Cellosolve ester such as methyl Cellosolve acetate; an aromatic hydrocarbon such toluene or xylene; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 1 to 300 mJ/cm². As discussed above, preferred exposure wavelengths include sub-200 nm such as 193 nm. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The following non-limiting example is illustrative of the invention.

EXAMPLE 1

Synthesis of Nitrogen-Containing Compound
(Compound 4 in Scheme A)

The synthesis of the title compound (Compound 4 in Scheme A) is described in the following Scheme A. The detailed synthetic procedures for each step are outlined below.

Part 1: Synthesis of Compound (2):
2-Amino-2-methyl-proane-1,3-diol (5 parts) and dodecanal (8.5 parts) were dissolved in 90/10 methylene chloride (20 parts), and (15 parts), separately. Dodecanal solution was added into 2-amino-2-methyl-proane-1,3-diol solution with stirring at room temperature. The mixture was stirred at room temperature overnight and used in next step without purification.

Part 2: Synthesis of Compound (3):
The above mixture was cooled in an ice bath. Sodium borohydrid (3.8 parts) was dissolved in 20 parts of 50/50 methylene chloride/methanol and added to the above mixture slowly. The resulting mixture was stirred at room temperature for 3 hr. Compound 3 was isolated by normal aqueous workup followed by removal of solvent.

Part 3: Synthesis of Compound (4):
9.3 Parts of compound (3) and 9.7 parts of di-tert-butyl carbonate were dissolved in 40 parts of ethyl acetate, which was treated with 6.8 Parts of triethanol nitrogen-containing. The mixture was stirred for four hours at room temperature. Compound 4 was isolated via silica gel chromatography using ethyl acetate as mobile phase.

EXAMPLE 2

Synthesis of Nitrogen-Containing Compound
(Compound 6 in Scheme B)

The synthesis of the title compound (Compound 6 in Scheme B) is described in the following Scheme B. The detailed synthetic procedures for each step are outlined below.

Scheme B Reaction 2

Synthesis of Compound (6)

Dissolve 5 parts of 2-amino-2-hydroxymethy-propane-1,3-diol in 70 parts of 1:1 methanol/tert-butanol mixed solvent. Dissolve 6.4 parts of Di-tert-butyl carbonate in 50 parts of melting tert-butanol. Add Di-tert-butyl carbonate/tert-butanol solution into 2-amino-2-hydroxymethy-propane-1,3-diol/1:1 methanol/tert-butanol solution slowly at room temperature and keep stirring overnight. Remove solvents. Re-crystallize by ethyl acetate.

EXAMPLE 3

Photoresist Preparation and Lithographic Processing

A photoresist of the invention is prepared by mixing the following components with amounts expressed as weight percent based on total weight of the resist compositions:

| Resist components | Amount (wt. %) |
|---|---|
| Resin binder | 15 |
| Photoacid generator | 4 |
| Nitrogen-containing compound | 0.5 |
| Solvent | 81 |

The resin binder is a terpolymer (2-methyl-2-adamantyl methacrylate/beta-hydroxy-gamma-butyrolactone methacrylate/cyano-norbornyl methacrylate). The photoacid generator is the compound t-butyl phenyl tetramethylene sulfonium perfluorobutanesulfonate. The nitrogen-containing compound is the Compound 4 of Scheme A shown above in Example 1 and as prepared in Example 1 above. The solvent component is propylene glycol methyl ether acetate admixed with cyclohexanone and ethyl lactate. The resin, PAG and nitrogen-containing compound components are admixed in the solvent component.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26N aqueous tetramethylammonium hydroxide solution to develop the imaged resist layer.

EXAMPLE 4

Photoresist Preparation and Lithographic Processing

A photoresist of the invention is prepared by mixing the following components with amounts expressed as weight percent based on total weight of the resist compositions:

| Resist components | Amount (wt. %) |
|---|---|
| Resin binder | 15 |
| Photoacid generator | 4 |
| Nitrogen-containing compound | 0.5 |
| Solvent | 81 |

The resin binder is a terpolymer (2-methyl-2-adamantyl methacrylate/beta-hydroxy-gamma-butyrolactone methacrylate/cyano-norbornyl methacrylate). The photoacid generator is the compound t-butyl phenyl tetramethylene sulfonium perfluorobutanesulfonate. The nitrogen-containing compound is the compound Compound 6 of Scheme B shown above in Example 2 and as prepared in Example 2 above. The solvent component is propylene glycol methyl ether acetate admixed with cyclohexanone and ethyl lactate. The resin, PAG and nitrogen-containing compound components are admixed in the solvent component.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26N aqueous tetramethylammonium hydroxide solution to develop the imaged resist layer.

EXAMPLE 5

Lithographic Results (Included Comparative Date)

Figure 1A:
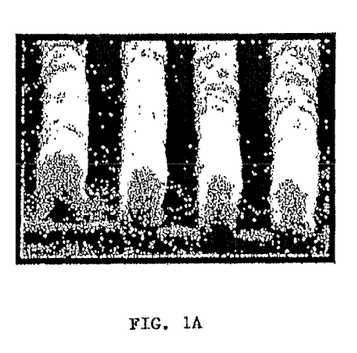
FIGS. 1A and 1B are SEMs that depict results of Example 5 which follows.

A photoresist (Photoresist 1) corresponding to the formulation of Example 3 was spincoated onto an organic bottom antireflective layer that had been coated over a 300 mm silicon wafer. The Photoresist 1 layer was softbaked to provide a dried layer thickness. An organic top coat was then applied over the photoresist. The Photoresist 1 layer was then patternwise immersion exposed at 193 nm ASML 1900i; 1.3 NA CQUAD 40° 0.98/0/78σ XY Polarization). Following exposure, the imaged Photoresist 1 layer was developed with 0.26N tetramethylammonium hydroxide aqueous developer. Scanning electron micrographs (SEM's) of the resulting developed Photoresist 1 is set forth at FIG. 1A of the drawings.

Figure 1B:
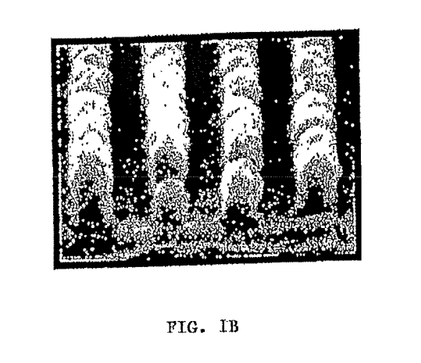

A comparative photoresist (Comparative Photoresist 1) corresponding to the formulation of Example 1, except that the nitrogen-containing compound contained a single hydroxyl group, was spincoated onto an organic bottom antireflective layer that had been coated over a 300 mm silicon wafer. The Comparative Photoresist 1 layer was softbaked to provide a dried layer thickness. An organic top coat was then applied over the photoresist. The Comparative Photoresist 1 layer was then patternwise immersion exposed at 193 nm ASML 1900i; !.3 NA CQUAD 40° 0.98/0/78σ XY Polarization). Following exposure, the imaged Comparative Photoresist 1 layer was developed with 0.26N tetramethylammonium hydroxide aqueous developer. Scanning electron micrographs (SEM's) of the resulting developed Comparative Photoresist 1 is set forth at FIG. 1B of the drawings. As can be seen from FIGS. 1A and 1B, Photoresist 1 provided a relief image with notably improved resolution (straighter and more even printed lines) relative to Comparative Photoresist 1.

EXAMPLE 6

Lithographic Results (Included Comparative Date)

Figure 2A:
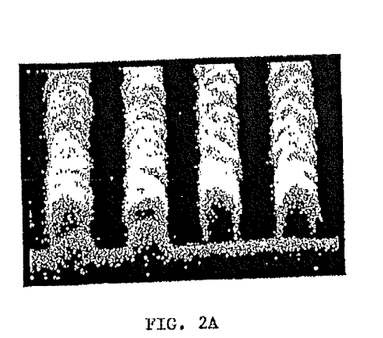
FIGS. 2A and 2B are SEMs that depict results of Example 6 which follows.

A photoresist (Photoresist 2) corresponding to the formulation of Example 4 was spincoated onto an organic bottom antireflective layer that had been coated over a 300 mm silicon wafer. The Photoresist 2 layer was softbaked to provide a dried layer thickness. An organic top coat was then applied over the photoresist. The Photoresist 2 layer was then patternwise immersion exposed at 193 nm ASML 1900i; 1.3 NA CQUAD 40° 0.98/0/78σ XY Polarization). Following exposure, the imaged Photoresist 2 layer was developed with 0.26N tetramethylammonium hydroxide aqueous developer. Scanning electron micrographs (SEM's) of the resulting developed Photoresist 2 is set forth at FIG. 2A of the drawings.

Figure 2B:
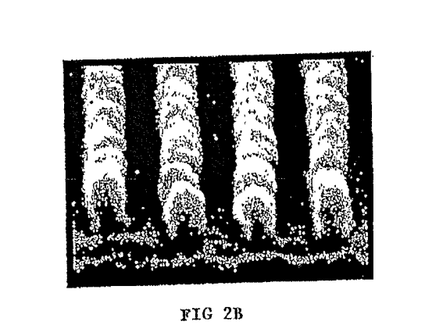

A comparative photoresist (Comparative Photoresist 2) corresponding to the formulation of Example 1, except that the nitrogen-containing compound contained a single hydroxyl group, was spincoated onto an organic bottom antireflective layer that had been coated over a 300 mm silicon wafer. The Comparative Photoresist 2 layer was softbaked to provide a dried layer thickness. An organic top coat was then applied over the photoresist. The Comparative Photoresist 2 layer was then patternwise immersion exposed at 193 nm ASML 1900i; !.3 NA CQUAD 40° 0.98/0/78σ XY Polarization). Following exposure, the imaged Comparative Photoresist 1 layer was developed with 0.26N tetramethylammonium hydroxide aqueous developer. Scanning electron micrographs (SEM's) of the resulting developed Comparative Photoresist 1 is set forth at FIG. 2B of the drawings. As can be seen from FIGS. 2A and 2B, Photoresist 2 provided a relief image with notably improved resolution (straighter and more even printed lines) relative to Comparative Photoresist 2.

What is claimed is:

1. A photoresist composition comprising:
   (a) one or more resins;
   (b) one or more photoacid generator compounds; and
   (c) one or more nitrogen-containing compounds that each comprise 1) two or more hydroxyl substituents and 2) one or more photoacid-labile ester groups and/or photoacid-labile acetal groups, with the exclusion of N-(t-butoxy carbonyl)diethanolamine.

2. The photoresist composition of claim 1 wherein the one or more of the nitrogen-containing compounds comprise a polymer.

3. The photoresist composition of claim 1 wherein the one or more of the nitrogen-containing compounds is non-polymeric.

4. The photoresist composition of claim 1 wherein the one or more nitrogen-containing compounds have a molecular weight of less than 2000.

5. The photoresist composition of claim 1 wherein one or more of the nitrogen-containing compounds is represented by one of the following Formula (I):

wherein $R^1$ and $R^2$ are the same or different and at least one of $R^1$ and $R^2$ is other than hydrogen, and together $R^1$ and $R^2$ comprise at least two hydroxyl groups, or $R^1$ and $R^2$ may be taken together to form a ring where the ring (including substituents thereof) comprises at least 2 hydroxy groups; and X comprises a photoacid-labile group.

6. The photoresist composition of claim 1 wherein one or more of the nitrogen-containing compounds comprise one or more of the following structures:

7. A method for forming a photoresist relief image comprising:

a) applying a coating layer of a photoresist composition of claim 1 on a substrate;

(b) exposing the photoresist coating layer to patterned activating radiation and developing the exposed photoresist layer to provide a relief image.

8. The photoresist composition of claim 1 wherein one or more of the nitrogen-containing compounds correspond to the following Formula (IIB):

(IIB)

wherein in Formula (IIB) $R^1$ and $R^2$ are the same or different and at least one of $R^1$ and $R^2$ is other than hydrogen, and together $R^1$ and $R^2$ comprise at least two hydroxyl groups, or $R^1$ and $R^2$ may be taken together to form a ring where the ring (including substituents thereof) comprises at least 2 hydroxy groups; and $R_1$, $R_2$ and $R_3$ each independently represent an optionally substituted straight, branched or cyclic group of 1 to 30 carbon atoms.

9. A photoresist composition comprising:

(a) one or more resins;

(b) one or more photoacid generator compounds; and (c) one or more nitrogen-containing compounds represented by one of the following Formula (I):

(I)

wherein $R^1$ and $R^2$ are the same or different and at least one of $R^1$ and $R^2$ is other than hydrogen, and wherein $R^1$ comprises at least two hydroxyl groups, or $R^2$ comprises at least two hydroxyl groups, or $R^1$ and $R^2$ are taken together to form a ring where the ring (including substituents thereof) comprises at least 2 hydroxy groups; and X comprises a photoacid-labile group.

10. The photoresist composition of claim 9 wherein $R^1$ comprises at least two hydroxyl groups.

11. The photoresist composition of claim 9 wherein $R^2$ comprises at least two hydroxyl groups.

12. The photoresist composition of claim 9 wherein $R^1$ is hydrogen and $R^2$ is a non-hydrogen group that comprises at least two hydroxyl groups.

13. The photoresist composition of claim 9 wherein $R^1$ and $R^2$ are taken together to form a cyclic structure.

14. The photoresist composition of claim 9 wherein one or more of the nitrogen-containing compounds correspond to the following Formula (IIC):

(IIC)

wherein $R_1$, $R_2$ and $R_3$ each independently represent an optionally substituted straight, branched or cyclic group of 1 to 30 carbon; $R_4$ represents hydrogen or a straight, branched or cyclic group of 1 to 30 carbon; m1, m2 and m3 are each independently an integer of 0 to 30; n1, n2 and n3 are each independently an integer of 0 or 1; at least two among n1, n2 and n3 are 1.

15. The photoresist composition of claim 9 wherein one or more of the nitrogen-containing compounds correspond to the following Formula (IID):

(IID)

wherein $R_1$, $R_2$ and $R_3$ each independently represent a straight, branched or cyclic group of 1 to 30 carbon; $R_4$ represents hydrogen or an optionally substituted straight, branched or cyclic group of 1 to 30 carbon; n is an integer of 1 to 30; and n is a positive integer e.g. from 1 to 20.

16. A method for forming a photoresist relief image comprising:

a) applying a coating layer of a photoresist composition of claim 9 on a substrate;

b) exposing the photoresist coating layer to patterned activating radiation and developing the exposed photoresist layer to provide a relief image.

17. A method for forming a photoresist relief image comprising:

a) applying a coating layer of a photoresist composition of claim 10 on a substrate;

b) exposing the photoresist coating layer to patterned activating radiation and developing the exposed photoresist layer to provide a relief image.

18. A method for forming a photoresist relief image comprising:

a) applying a coating layer of a photoresist composition of claim 11 on a substrate;

b) exposing the photoresist coating layer to patterned activating radiation and developing the exposed photoresist layer to provide a relief image.

19. A method for forming a photoresist relief image comprising:

a) applying a coating layer of a photoresist composition of claim 12 on a substrate;

b) exposing the photoresist coating layer to patterned activating radiation and developing the exposed photoresist layer to provide a relief image.

20. A method for forming a photoresist relief image comprising:
   a) applying a coating layer of a photoresist composition of claim 13 on a substrate;
   b) exposing the photoresist coating layer to patterned activating radiation and developing the exposed photoresist layer to provide a relief image.

21. A method for forming a photoresist relief image comprising:
   a) applying a coating layer of a photoresist composition of claim 14 on a substrate;
   b) exposing the photoresist coating layer to patterned activating radiation and developing the exposed photoresist layer to provide a relief image.

22. A method for forming a photoresist relief image comprising:
   a) applying a coating layer of a photoresist composition of claim 15 on a substrate;
   b) exposing the photoresist coating layer to patterned activating radiation and developing the exposed photoresist layer to provide a relief image.

* * * * *